(12) United States Patent
Doerr et al.

(10) Patent No.: US 7,769,453 B2
(45) Date of Patent: Aug. 3, 2010

(54) IMPLANTABLE BATTERY-OPERATED ELECTROSTIMULATION DEVICE

(75) Inventors: Thomas Doerr, Berlin (DE); Torsten Lang, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 390 days.

(21) Appl. No.: 11/693,973

(22) Filed: Mar. 30, 2007

(65) Prior Publication Data
US 2007/0250131 A1 Oct. 25, 2007

(30) Foreign Application Priority Data
Apr. 25, 2006 (DE) .................... 10 2006 019 606

(51) Int. Cl.
*A61N 1/37* (2006.01)
(52) U.S. Cl. .................... 607/27; 607/29; 607/32; 607/60; 607/59
(58) Field of Classification Search ........... 607/1–30, 607/31–32
See application file for complete search history.

(56) References Cited

U.S. PATENT DOCUMENTS

| | | | |
|---|---|---|---|
| 4,488,555 A | 12/1984 | Imran | |
| 5,370,668 A | 12/1994 | Shelton | |
| 6,016,448 A | 1/2000 | Busacker | |
| 6,434,426 B1 * | 8/2002 | Munneke et al. | 607/27 |
| 2003/0065366 A1 * | 4/2003 | Merritt et al. | 607/27 |
| 2004/0030358 A1 * | 2/2004 | Rueter et al. | 607/27 |
| 2006/0020290 A1 | 1/2006 | Degroot | |
| 2006/0064136 A1 * | 3/2006 | Wang | 607/27 |

FOREIGN PATENT DOCUMENTS

| | | |
|---|---|---|
| DE | 19930263 A1 | 12/2000 |
| EP | 0750921 | 1/1997 |
| WO | WO 02/057994 | 7/2002 |

OTHER PUBLICATIONS

German Search Report, dated Jan. 10, 2007.
European Search Report, dated Feb. 6, 2008.

* cited by examiner

*Primary Examiner*—Carl H Layno
*Assistant Examiner*—Paula J Stice
(74) *Attorney, Agent, or Firm*—ARC IP Law, PC; Joseph J. Mayo

(57) ABSTRACT

The present invention relates to an implantable battery-operated electrostimulation device (10), particularly for stimulating a heart, having a telemetry unit (11) for wireless data transmission between the electrostimulation device (10) and an external device (21), a control unit (15), which is connected to the telemetry unit (11) and is implemented to trigger a telemetric data transmission, a battery (13) for the power supply of the electrical components of the implant, such as the telemetry unit and the control unit, and a self-test unit, which is implemented to register the functional state of the electrostimulation device and independently detect acute or imminent malfunctions, the self-test unit (17) being connected to the control unit and the control unit being implemented to trigger a data transmission using data on the functional state of the electrostimulation device if an acute or imminent malfunction is detected.

3 Claims, 1 Drawing Sheet

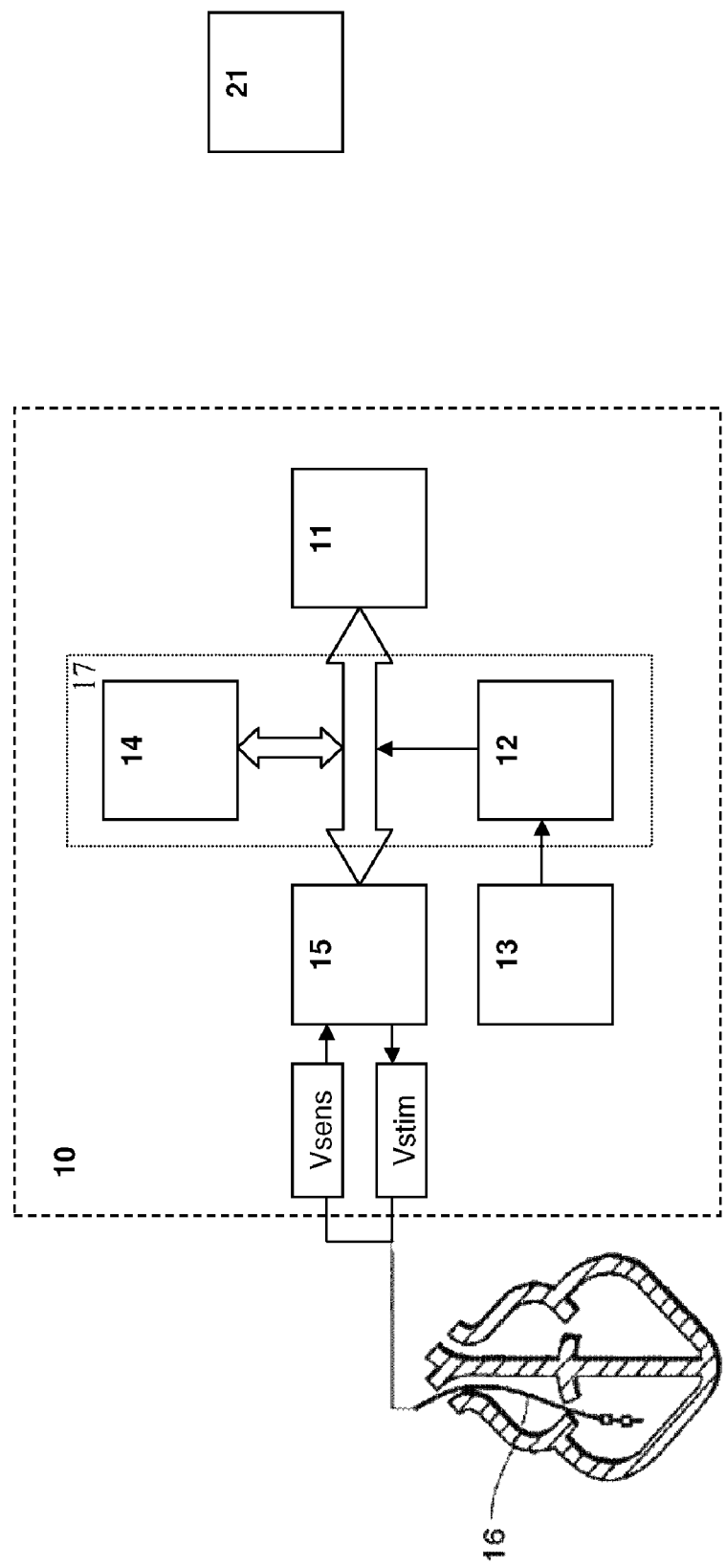

IMPLANTABLE BATTERY-OPERATED ELECTROSTIMULATION DEVICE

This application takes priority from German Patent Application DE 10 2006 019 606.6 filed 25 Apr. 2006, the specification of which is hereby incorporated herein by reference.

BACKGROUND OF THE INVENTION

1. Field of the Invention

The present invention relates to an implantable battery-operated electrostimulation device, referred to in the following as an implant, having a telemetry unit for wireless data transmission from the implant to an external device and possibly vice versa.

2. Description of the Related Art

Implants of this type allow telemetric remote monitoring of the implant by transmitting data from the implant via a service center to an attending physician, for example. The data may be physiological data, which the implant has recorded on the body of a patient, or technical data, which relates to the operation and control of the implant. Typical implants of this type are cardiac pacemakers or cardioverters/defibrillators.

In known implants, telemetric data transmission is triggered either manually (i.e., the patient must activate the query of the implant with subsequent data remote transmission) or automatically.

In battery-powered implants, the problem exists in principle that all functions of the implant are powered via a battery, which may run out. Therefore, the treatment functions of the implant, i.e., delivering stimulation pulses or defibrillation shocks, for example, are already tailored in such a way that they require as little energy as possible, without omitting a needed treatment. The mean current consumption of the implant is thus strongly a function of the need of the patient for treatment.

The telemetry functions of the implant also take the limited battery capacity into consideration.

Known manual systems do not trigger data transmission themselves, i.e., even when a specific operating state of the implant or an automatically recognized pathological state of the patient makes the intervention of a physician or technician obvious. Rather, the patient is to have the possibility, in case of feeling unwell, of informing a physician or service center by manually triggering a data transmission himself, in order to receive medical attention if necessary. If the patient has triggered the data transmission, data relating to the operating state of the implant, such as battery exhaustion or a recognized device error, is also transmitted telemetrically to the physician.

Known automatic systems automatically transmit the physiological data to the physician after detecting a pathological state, for example. The implant turns itself off upon reaching battery exhaustion or in the event of a recognized device error in the course of a cyclic self-test.

SUMMARY OF THE INVENTION

The present invention is based on the object of increasing the operational reliability of the implants.

This object is achieved according to the present invention by an implantable, battery-operated electrostimulation device, which has a telemetry unit, a control unit, which is at least indirectly connected to the telemetry unit, a battery for power supply, and a self-test unit. The control unit is implemented to trigger a telemetric data transmission via the telemetry unit.

The self-test unit is implemented to register the functional state of the electrostimulation device and automatically detect acute or imminent malfunctions and subsequently trigger a telemetric data transmission via the telemetry unit directly or using the control unit. The self-test unit and control unit are connected to one another and either the self-test unit or the control unit triggers a data transmission having data on the functional state of the electrostimulation device if an acute or imminent malfunction of the implant is detected. The experience is based on the finding that in particular in implantable cardioverters/defibrillators as electrostimulators, sudden, unforeseeable battery exhaustion may occur if such a cardioverter/defibrillator must deliver a large number of discharges within a short time. This may occur as a result of a frequently reoccurring life-threatening arrhythmia, which is also referred to as an electric storm. Since this event and the operating state of the electrostimulation device resulting therefrom do not occur very frequently, a large amount of attention is possibly not given thereto in typical electrostimulation devices. Precisely the electrostimulation device exhausted by such reoccurring, life-threatening arrhythmias and the patient wearing the electrostimulation device require immediate attention of the physician. In this connection, the electrostimulation device according to the present invention advantageously allows the physician to be informed immediately and automatically by the electrostimulation device about its operating state.

In a preferred embodiment variation of the present invention, the self-test unit has a battery monitoring unit which is implemented to register the exhaustion state of the battery and, either directly or via the control unit, to trigger a data transmission using data on the exhaustion state of the battery in the case of a final exhaustion of the battery which will occur soon.

Either the battery monitoring unit itself or the control unit connected thereto is preferably implemented to detect a state of the battery exhaustion in which the remaining residual charge of the battery is sufficient so that the telemetry unit may automatically transmit at least one more message having information about the battery exhaustion to an external device. It is thus ensured that a possibly decisive data transmission which informs the physician is possible using the residual battery charge.

Alternatively or additionally to the battery monitoring unit, a preferred electrostimulation device has an error recognition unit for recognizing device errors as a part of the self-test unit. This error recognition unit is connected to the telemetry unit either directly or via the control unit and implemented, in case of a recognized device error, to switch the electrostimulation device over into a safety mode and to automatically trigger at least one data transmission using the information about the activation of the safety mode in this safety mode. An electrostimulation device of this type may not only register the exhaustion state of its battery, but rather also other device errors. In addition, the electrostimulation device not only automatically communicates device errors of this type for data transmission via the telemetry unit, but rather also activates a safety mode, which ensures the basic functions of the electrostimulation device and, in this way, allows the electrostimulation device to be able to still execute safety-relevant basic functions in spite of a device error.

BRIEF DESCRIPTION OF THE DRAWINGS

The present invention will now be explained in greater detail on the basis of an exemplary embodiment with reference to the FIGURE:

FIG. 1 shows a schematic block diagram of an electrostimulation device according to the present invention.

DETAILED DESCRIPTION OF THE INVENTION

In the FIGURE, the stimulation device is represented as a dashed box 10. It may be seen that the stimulation device 10, such as a cardiac pacemaker and cardioverter/defibrillator, is connected to an electrode line 16, which, in the implanted electrostimulation device 10 in the exemplary case, ends in the right ventricle of a heart.

This electrode line 16 is connected to a control unit 15 in the interior of the electrostimulation device 10 in the example shown via a ventricular stimulation unit Vstim and a ventricular sensing unit Vsens.

In addition, the electrostimulation device may have the typical components of an implantable cardiac pacemaker or an implantable cardioverter/defibrillator, namely, in the case of a dual chamber pacemaker, additionally an atrial stimulation unit and an atrial sensing unit, to be able to deliver stimulation pulses to the atrium as well and, furthermore, detect natural atrial contractions on the basis of the analysis of electrical potential curves in the heart (registered via an intracardial electrocardiogram). In the case of a cardioverter/defibrillator, the control unit additionally comprises an arrhythmia detector and a defibrillation shock generator. In the FIGURE, a ventricular sensing unit Vsense and a ventricular stimulation unit Vstim are shown, which are connected to the control unit 15.

The control unit 15 is connected via a bus to a telemetry unit 11, in order to transmit at least data from the electrostimulation device 10 to an external device 21, such as a patient device or a relay station, in this way. This data is typically physiological data that the electrostimulation device 10 has recorded and is transmitted via patient device 21 or relay station 21 to a central service station for evaluation by physician.

A battery 13 supplies all electrical components of the electrostimulation device 10 with electrical power. In addition, the battery 13 is connected to a battery monitoring unit 12, which is implemented to monitor the charge state of the battery 13 continuously or at regular intervals, in order to allow the exhaustion state of the battery 13 to be registered in this way. The exhaustion state may be registered by the battery monitoring unit 12 itself, or by the control unit 15, which is supplied with appropriate data for this purpose via the battery monitoring unit.

In the case of an acute exhaustion state of the battery 13, either the battery monitoring unit 12 itself or the control unit 15 triggers a data transmission via the telemetry unit 11. The transmitted data contains a signal which identifies the battery exhaustion state and signals that a final exhaustion of the battery 13 will occur soon.

The battery monitoring unit 12 or the control unit 15 is implemented for this purpose in such a way that it triggers data transmission using data on the exhaustion state of the battery when the charge state of the battery 13 still permits such a data transmission, i.e., before the final exhaustion. It is thus ensured that the remaining charge of the battery 13 is sufficient for the telemetry unit 11 to allow the data transmission using the data on the exhaustion state of the battery.

In addition, the electrostimulation device 10 has an error recognition unit 14 for recognizing device errors. The error recognition unit 14 is connected directly to the control unit 15 and implemented for the purpose of checking the data transmitted by the control unit 15 for plausibility. In the case of data inconsistency, the error recognition unit 14 triggers an error signal, which causes the electrostimulation device 10 to be switched over into a safety mode, in which operation of the essential functions of the electrostimulation device 10 is ensured by robust backup components. In addition, the error signal causes a data transmission via the telemetry unit 11. In this data transmission, the telemetry unit 11 transmits a signal which identifies the changeover of the electrostimulation device 10 into the safety mode. In this way, the electrostimulation device 10 is capable of automatically and independently informing an attending physician, for example, that the electrostimulation device 10 has recognized a device error in the course of a self-test by the error recognition unit 14 and has switched over into the safety mode.

In this way, the battery monitoring unit 12 and the error recognition unit 14 form a self-test unit 17, which is implemented for the purpose of regularly registering the operating state of the electrostimulation device 10, in particular in regard to possible device errors and in regard to the charge state and/or exhaustion state of the battery 13. The self-test unit triggers an appropriate data transmission via the telemetry unit 11 in case of a recognized device error or in case of a recognized exhaustion state of the battery, directly or using the control unit 15. In this data transmission, information about the device state of the electrostimulation device 10 is transmitted automatically.

What is claimed is:

1. An implantable battery operated electrostimulation device (10), for stimulating a heart comprising:
   a telemetry unit (11) for wireless data transmission between said implantable battery operated electrostimulation device (10) and an external device (21);
   a control unit (15), which is connected to said telemetry unit (11) and configured to trigger said wireless data transmission;
   a battery (13) to supply power for electrical components of said implantable battery operated electrostimulation device including said telemetry unit and said control unit;
   a self-test unit (17), configured to register a functional state of said implantable battery operated electrostimulation device and independently detect acute or imminent malfunctions of said implantable battery operated electrostimulation device;
   wherein said self-test unit (17) is connected to said control unit and is configured to automatically trigger said wireless data transmission through said telemetry unit to an external device (21) without receipt of an interrogation request from said external device (21) wherein said wireless data transmission comprises data on said functional state of said implantable battery operated electrostimulation device if said acute or imminent malfunctions are detected; and,
   wherein said self-test unit comprises a battery monitoring unit (12), configured to register an exhaustion state of said battery and, in case of a final exhaustion of said battery to occur soon;
      trigger said wireless data transmission comprising data on said exhaustion state of said battery directly or via said control unit;
      wherein said battery monitoring unit or said control unit is configured to detect a state of battery exhaustion, while a remaining residual charge of said battery (13) is sufficient so that said telemet unit automatically transmits at least one further message comprising information about said battery exhaustion to said external device (21) and wherein said battery monitoring unit or said control unit does not command said telemetry unit to transmit said at least one further message if said residual charge of said battery (13) is insufficient to transmit said at least one further message.

2. An implantable battery operated electrostimulation device (10), for stimulating a heart comprising:
- a telemetry unit (11) for wireless data transmission between said implantable battery operated electrostimulation device (10) and an external device (21);
- data within said implantable battery operated electrostimulation device (10);
- a control unit (15), which is connected to said telemetry unit (11) and configured to trigger said wireless data transmission;
- a battery (13) to supply power for electrical components of said implantable battery operated electrostimulation device including said telemetry unit and said control unit;
- a self-test unit (17), configured to register a functional state of said implantable battery operated electrostimulation device and independently detect acute or imminent malfunctions of said implantable battery operated electrostimulation device;
- wherein said self-test unit (17) is connected to said control unit and is configured to automatically trigger said wireless data transmission through said telemetry unit to an external device (21) without receipt of an interrogation request from said external device (21) wherein said wireless data transmission comprises data on said functional state of said implantable battery operated electrostimulation device if said acute or imminent malfunctions are detected irrespective of an amount of said data within said implantable battery operated electrostimulation device (10);
- wherein said self-test unit (17) has an error recognition unit (14) configured to recognize device errors, which is connected to said control unit (15), and either said error recognition unit (14) or said control unit (15) is configured to, in case of a recognized device error, to switch said electrostimulation device over into a safety mode, and in said safety mode, to automatically trigger at least one wireless data transmission using information about an activation of said safety mode.

3. An implantable battery operated electrostimulation device (10), for stimulating a heart comprising:
- a telemetry unit (11) for wireless data transmission between said implantable battery operated electrostimulation device (10) and an external device (21);
- a control unit (15), which is connected to said telemetry unit (11) and configured to trigger said wireless data transmission;
- a battery (13) to supply power for electrical components of said implantable battery operated electrostimulation device including said telemetry unit and said control unit;
- a self-test unit (17), configured to register a functional state of said implantable battery operated electrostimulation device and independently detect acute or imminent malfunctions of said implantable battery operated electrostimulation device;
- wherein said self-test unit (17) is connected to said control unit and is configured to automatically trigger said wireless data transmission through said telemetry unit to an external device (21) without receipt of an interrogation request from said external device (21) wherein said wireless data transmission comprises data on said functional state of said implantable battery operated electrostimulation device if said acute or imminent malfunctions are detected;
- wherein said self-test unit comprises a battery monitoring unit (12), configured to
  - register an exhaustion state of said battery and, in case of a final exhaustion of said battery to occur soon;
  - trigger said wireless data transmission comprising data on said exhaustion state of said battery directly or via said control unit;
  - wherein said battery monitoring unit or said control unit is configured to detect a state of battery exhaustion, while a remaining residual charge of said battery (13) is sufficient so that said telemetry unit automatically transmits at least one further message comprising information about said battery exhaustion to said external device (21) and wherein said battery monitoring unit or said control unit do not command said telemetry unit to transmit said at least one further message if said residual charge of said battery (13) is insufficient to transmit said at least one further message; and,
- wherein said self-test unit (17) further comprises an error recognition unit (14) configured to recognize device errors, wherein said error recognition unit is connected to said control unit (15), and either said error recognition unit (14) or said control unit (15), in case of a recognized device error, is configured to
  - switch said electrostimulation device over into a safety mode, and in said safety mode, to automatically trigger at least one wireless data transmission using information about an activation of said safety mode while a remaining residual charge of said battery (13) is high enough so that said telemetry unit may still automatically transmit at least one further message comprising information about said battery exhaustion to said external device (21).

* * * * *